United States Patent
Wolf et al.

(10) Patent No.: US 7,596,287 B2
(45) Date of Patent: Sep. 29, 2009

(54) METHOD AND DEVICE FOR THE THREE-DIMENSIONAL DETERMINATION AND DIGITIZATION OF A PLASTER- OR POSITIVE-MODEL

(75) Inventors: Dietrich Wolf, Hanau (DE); Stefan Fecher, Johannesberg (DE)

(73) Assignee: DeguDent GmbH, Hanau (DE)

( * ) Notice: Subject to any disclaimer, the term of this patent is extended or adjusted under 35 U.S.C. 154(b) by 1182 days.

(21) Appl. No.: 10/480,796

(22) PCT Filed: Jul. 2, 2002

(86) PCT No.: PCT/EP02/07283

§ 371 (c)(1),
(2), (4) Date: Dec. 19, 2003

(87) PCT Pub. No.: WO03/007835

PCT Pub. Date: Jan. 30, 2003

(65) Prior Publication Data

US 2004/0151367 A1    Aug. 5, 2004

(30) Foreign Application Priority Data

Jul. 13, 2001    (DE)    ............................. 101 33 568

(51) Int. Cl.
*G06K 9/00* (2006.01)
*G06K 7/00* (2006.01)
(52) U.S. Cl. ...................................... 382/312; 382/128
(58) Field of Classification Search .................. 382/312
See application file for complete search history.

(56) References Cited

U.S. PATENT DOCUMENTS

| | | | | |
|---|---|---|---|---|
| 5,781,652 A * | 7/1998 | Pratt | ............................ | 382/128 |
| 5,953,137 A | 9/1999 | Sirat et al. | | |
| 6,217,334 B1 * | 4/2001 | Hultgren | ...................... | 433/215 |
| 6,236,743 B1 * | 5/2001 | Pratt | ............................ | 382/128 |
| 6,690,498 B2 * | 2/2004 | Shim | ........................... | 359/216 |
| 6,757,088 B2 * | 6/2004 | Shim | ........................... | 359/196 |
| 6,905,293 B1 * | 6/2005 | Filser et al. | .................... | 409/84 |
| 7,068,825 B2 * | 6/2006 | Rubbert et al. | ............... | 382/128 |

FOREIGN PATENT DOCUMENTS

| | | |
|---|---|---|
| DE | 4301538 | 7/1994 |
| DE | 19710273 | 8/1998 |
| DE | 10029256 | 11/2000 |
| EP | 1106146 | 6/2001 |

* cited by examiner

*Primary Examiner*—Yuzhen Ge
(74) *Attorney, Agent, or Firm*—Dennison, Schultz & MacDonald

(57) ABSTRACT

A method for the three-dimensional determination and digitization of a plaster- or positive-model, in particular for the production of replacement teeth, with improved handling and costs. According to the method, a plaster- or positive-model is clamped in a mounting with a defined orientation and irradiated by means of a radiation source; the radiation reflected by the plaster- or positive-model is recorded and evaluated by a scanning unit. Separation information is generated, and defined movement of the plaster- or positive-model relative to the radiation source takes place along an axis (y), approximately perpendicular to the direction of radiation and linking the displacement with the separation information. The invention also relates to a device for carrying out the method.

8 Claims, 3 Drawing Sheets

METHOD AND DEVICE FOR THE THREE-DIMENSIONAL DETERMINATION AND DIGITIZATION OF A PLASTER-OR POSITIVE-MODEL

The invention relates to a method and a device for the three-dimensional mapping and digitization of a plaster or positive model for producing dental prostheses.

In particular, the invention relates to the field of producing basic structures for dental prostheses, in particular for dental crowns and/or bridges for fastening to prepared natural and/or artificial tooth stumps or the like.

A number of devices and methods for producing artificial dental bridges and crowns are known. Generally, after the dental preparation in which the teeth used for anchoring are prepared by grinding for receiving a crown or bridge or for which, e.g. a pin is implanted, an impression of the tooth stump, the surrounding area and jaw is made. This is usually done with silicone sealing compounds, but other materials are also known.

A so-called master model can be made from the impression (shows the situation in the patient's mouth negatively) by means of a plaster cast. This model shows the situation in the patient's mouth positively. In this model, the dental technician with his handicraft skills fashions a model of the basic structure of the dental prosthesis from wax or from plastic which melts at a low temperature or hardens in a polymerizing manner (positive model). In this case, the dental technician can also take the counter occlusion of the other jaw into account by means of the plaster model in hand.

Traditionally, the model produced by the dental technician is embedded and melted in heat-resistant substances. The basic structure can be made of in conventional metal dental alloys by precision casting in the mold thus produced.

For cosmetic reasons, a facing in ceramic or plastic is usually also made, at least in the area of the front teeth is known from WO 99/47065 to completely digitalize the outer and inner surface after a wax model (positive model) has been formed. A model which inadequately reflects the situation in the patient's mouth is then mathematically completed with respect to the three-dimensional outer and inner surface. The result of the digitization and a calculated supplementation should represent a digital description of the complete surface of the basic structure of the prosthesis to be produced. The positive model can thereby be turned in steps of up to 180° to digitalize the occlusively and cavitally accessible surfaces. The digitization described in the embodiment in WO 99/47065 of a wax model (positive model) of a tooth bridge construction should take place by sinuous line scanning of the wax body from two sides by the positive model being clamped between two waves.

The digitization is thereby accomplished mechanically or optically. For this purpose, reference is made to methods for digitization in the mouth of a patient on a prepared tooth stump or to models which, for example, are known from U.S. Pat. No. 4,182,312 with respect to a mechanical digitization and from EP 0 054 785 A1 with respect to an optical digitization.

The fundamental disadvantage of the mechanical digitization known from U.S. Pat. No. 4,182,312 is in the fixing of the mechanical scanning device to the patient, since the scanning is to take place directly in the oral cavity of the patient. The secure handling of the device in the narrow oral cavity is equally problematic. A processing machine for producing dental prostheses should be controlled directly with the scanning of teeth and surrounding tissue as in a duplicating mill.

To this end, a probe having a transmission rod securely fixed to it must be moved by the dentist over the surfaces in the patient's mouth that are of interest. A complete detection of the surface requires very many scanning movements, which is very stressful for the patient due to the time needed. Furthermore, the probe tips must be changed, depending on the shape of the processing tool.

With the method described in EP 0 054 785 A1, an image recording head is to be inserted into a patient's mouth. This image recording head is to detect a three-dimensional image of a tooth cavity or the like. For this purpose, the image data is to be displayed on a computer screen, so that a dentist can check to see whether the positioning of the image recording head enables a sufficiently accurate image. If necessary, the more favorable positioning of the image recording head can be changed accordingly.

When a proper position has been obtained, a three-dimensional image of the tooth cavity or the like should—without further explanation—be formed spatially true to size. The appropriate data is then to be completed by interpolation and manual processing of the data set along the lines of a CAD construction, until a corresponding dental prosthesis body has been completely formed. The corresponding data should then be used to work on a suitable blank in order to produce a suitable dental prosthesis directly from the image while avoiding the aforementioned skilled production steps.

The awkward manipulation with the camera in the patient's mouth was also found to be disadvantageous in practice with this method, and in particular, it requires great discipline on the part of the patient.

Furthermore, as described in the aforementioned document, it is necessary to coat the tooth which is to be mapped with a powder to obtain defined reflection conditions, since the natural dental material has translucent properties. Due to the translucent properties, light could otherwise penetrate partially uncontrolled into the tooth stump to be measured and perhaps be reflected in deeper layers which would result in an inaccurate result. However, the coating with a reflection powder simultaneously increases the inaccuracy by the application of the powder which will inherently and, based on the restricted conditions in the patient's mouth, always be irregular in practice. The limited resolving power of the image recorder and the difficult lighting conditions in the mouth to be mapped are also disadvantageous.

Furthermore, other methods for the optical digitization of workpieces in the field of dental technology are also known in which a clamped workpiece is shown in typically 8 to 16 different angular positions and the data thus obtained is mathematically compiled to form a volume model. In addition to high demands for accuracy of the devices used, this method causes substantial computing requirements with considerable sources of error due to the many and, thus, long measurements. On the whole, therefore, these methods are very expensive and time consuming.

A method and an arrangement for the non-contact three-dimensional measurement of denture models is known from DE 43 01 538 A1. For this purpose, the object to be measured is placed on a rotary table in order to measure it according to the triangulation principle.

A drill template for implanting artificial teeth by means of CAD/CAM technology is produced by laser scanning of a working model according to DE 100 29 256 A1.

A machine tool as well as a method for producing basic structures for dental prostheses is known from WO 01/39691 A1. For this purpose, a dental preparatory model of the basic structure is preferably scanned in a tactile manner to produce, from the digitization data thereby obtained, a blank for producing the basic structure. For the scanning, the preparatory model can be set in two positions turned by 180°.

The object of the invention is to provide an improved method, especially with respect to handling and cost efficiency, for mapping a plaster or positive model and a device for carrying out the method.

According to the invention, the object is essentially solved by:

clamping the plaster or positive model in a mounting which is rotatable about an axis of rotation in a defined orientation;

irradiation of the plaster or positive model by means of a radiation source and receiving the radiation reflected by the plaster or positive model;

evaluating the reflected radiation by a scanning unit and generating a distance information;

defined movement of the plaster or positive model relative to the radiation source along a plane and/or first axis (y) which extends perpendicular or almost perpendicular to the direction of radiation;

linking a signal for detection of the rotation with the path and distance information for forming a three-dimensional volume model of the plaster or positive model, whereby the distance between the mounting and scanning unit in direction of the optical axis (z axis) of the scanning unit remains unchanged or essentially unchanged during the digitization of the plaster or positive model along a scanning path s, where $s \geq 1$ mm.

In particular, the scanning path s corresponds to the entire or almost the entire scanning distance along a side of the model to be scanned. A turning is not required for the measurement and digitization of a plaster model. With a positive model, it is necessary to turn it by approximately 180° about the axis of rotation of the mounting, which extends perpendicular to the direction of radiation.

With the method according to the invention, very accurate results can be obtained with relatively simple constructions, in addition to which the method is not very prone to error sources. Furthermore, the computational effort for forming a data model of the body to be mapped is much less compared to the known methods since a plurality of different views no longer have to be mathematically interlinked, given that the positive model is measured in only two positions displaced by 180° and the plaster model only in one position. Furthermore, the distance between the mounting or the plane mounted by it or a plane passing through the axis of rotation and the scanning unit, in particular when scanning a side, remains constant or almost constant, at least however in a direction of scanning along the plaster or positve model or along a scanning path.

A software for realizing the data processing can be created substantially more easily with this measure, as a result of which the speed of operation increases, the hardware requirements are reduced in favour of a more advantageous price and, due to the simpler structure of the software, the danger of programming and calculating errors is considerably reduced.

In an especially advantageous embodiment, the radiation is performed by a line scanner. By designing the method of the invention in this manner, only a mechanical movement in one axis has to be carried out for the three-dimensional digitization of a body or its surface, as a result of which the equipment requirement can be even further reduced and lowered in cost and, at the same time, possible errors are reduced by mechanical tolerances.

In particular due to the currently still moderate resolving power of line scanners, however, it can also be advantageous for obtaining a high accuracy if the radiation takes place by a laser with an almost point-like beam.

In this case, it is especially advantageous if the method also comprises the step of a defined movement of the body relative to the radiation source along a second axis almost perpendicular to the direction of radiation and linking the second travel path with the scanning information and the first path.

To determine absolute values of height information of the body, it is advantageous if the distance information is standardized to a reference point of the body, in particular, if the reference point is almost that point of the body which delivers the lowest distance value, which is advantageously ascertained by a preliminary run-through of the method. Absolute information about the height of the body can be read directly from the data thus obtained which can e.g. be used to select the blank.

Furthermore, according to the invention, the object is solved by a device comprising a mounting for accommodating a plaster or postive model to be mapped and digitalized, a scanning unit for optically scanning the plaster or positive model, the mounting with the plaster or positive model being diplaceable in at least one direction relative to, and at a right angle or almost at a right angle to, the optical axis of the scanning unit, and a device for detecting the path of the mounting with the plaster or positive model which is rotatable at a right angle about the optical axis by at least 180° or almost 180° in the at least one direction, whereby the scanning unit comprises a CCD image recorder, a birefractive crystal and an objective in the ray path. The possibility of turning the mounting is not required when measuring and digitalizing a plaster model.

In an especially advantageous embodiment of the device, the scanning unit also comprises a laser diode as well as a device for the imaging of the light of the laser diode into the path of rays of the scanning unit.

Further details, advantages and features of the invention can be found not only in the claims, in the features to be found therein—separately and/or in combination—but also in the following description of the preferred embodiments found in the drawings, in which:

Figure 1:
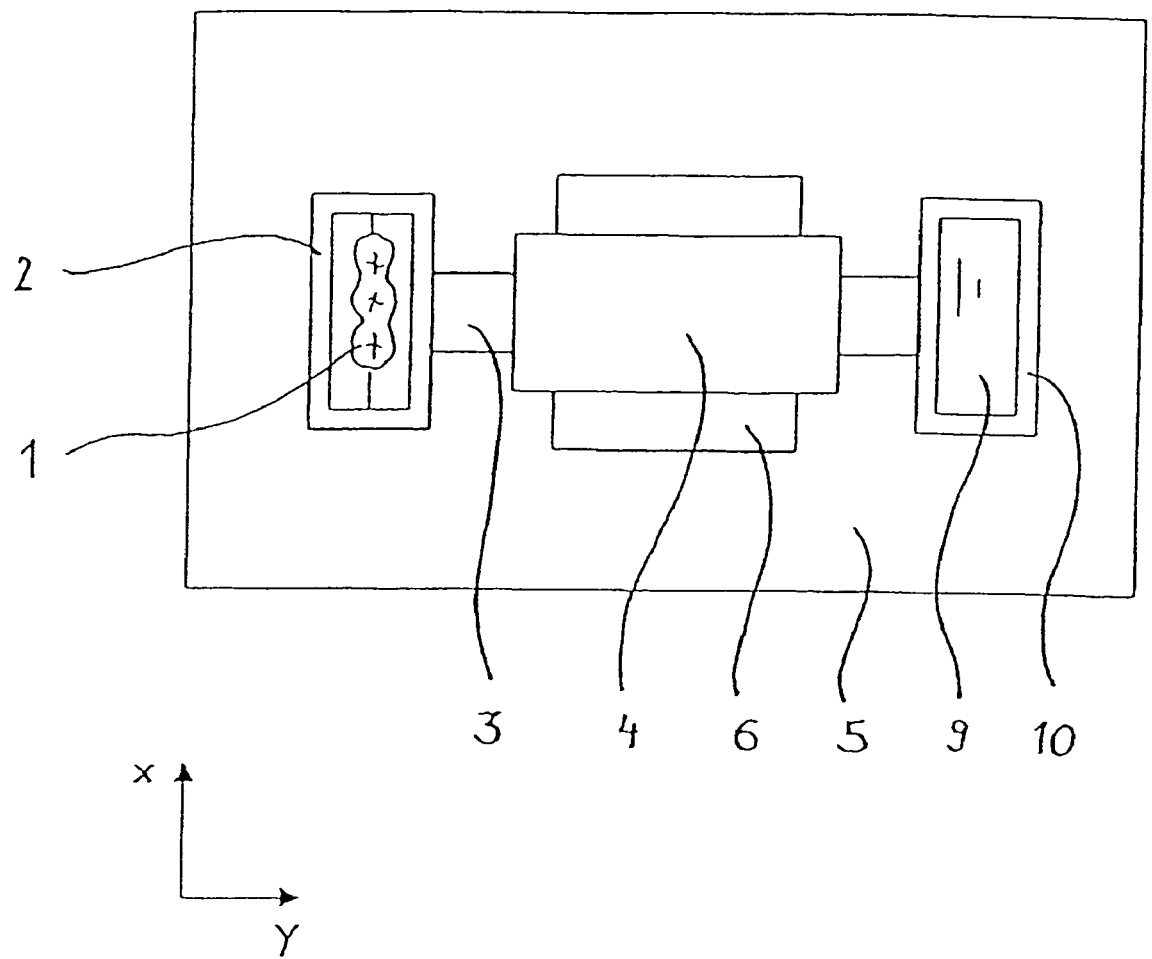
FIG. 1 shows a schematic view of a device for carrying out the method according to the invention.
Figure 2:
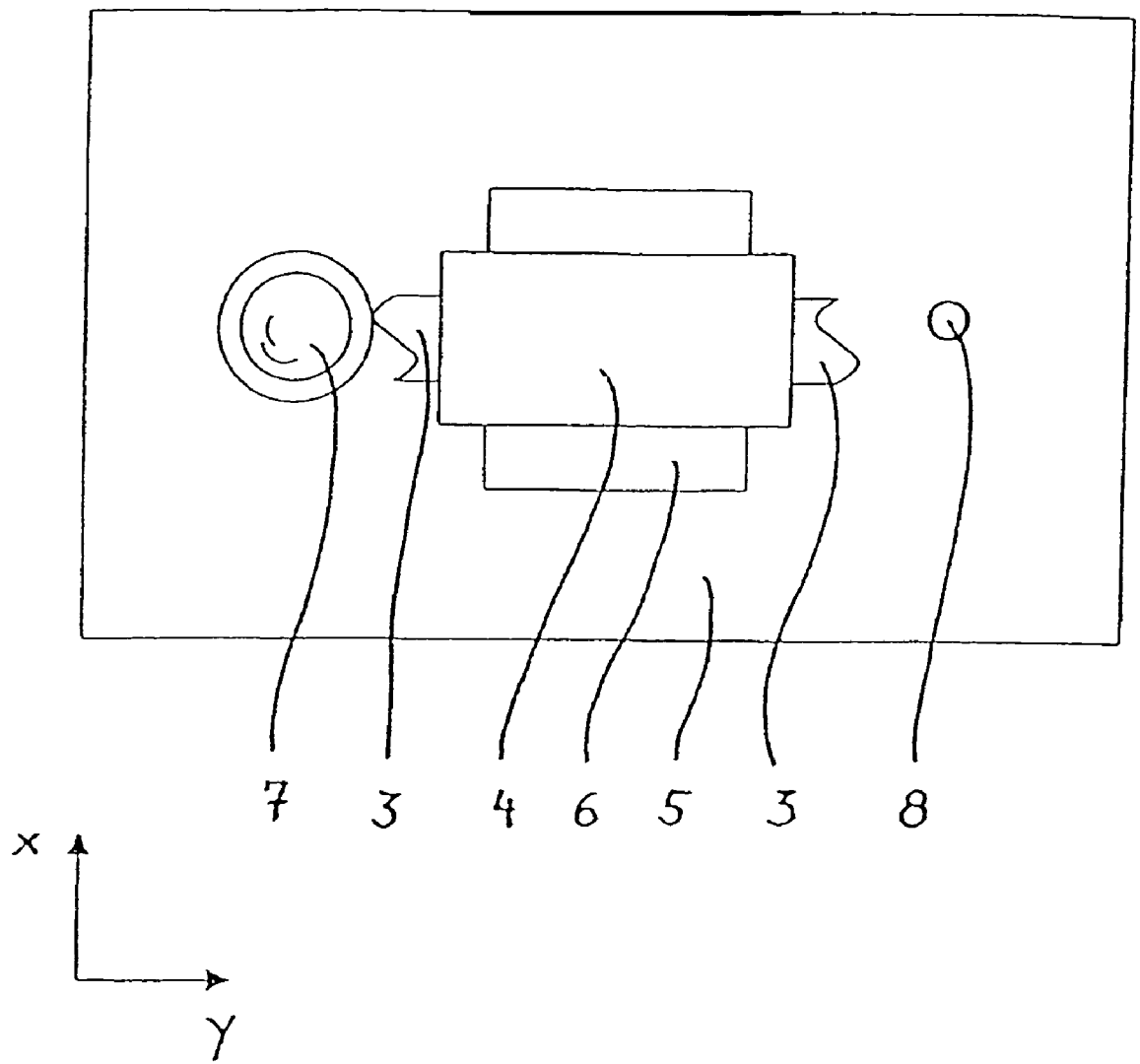
FIG. 2 shows the device from FIG. 1, in which each of the mountings have been omitted, so that the optical scanning unit and the cutting tool can be seen.
Figure 3:
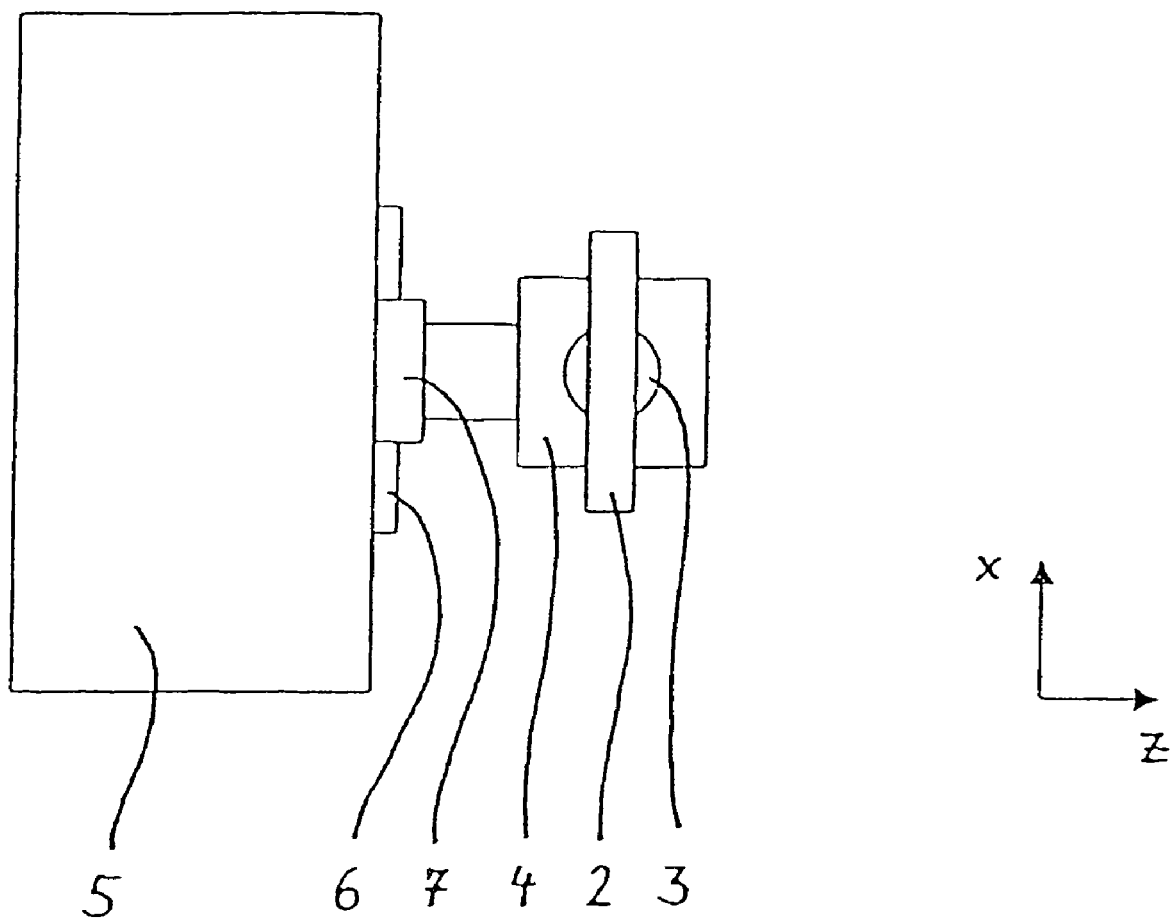
FIG. 3 shows a simplified side view of the device of FIGS. 1 and 2.

The orientations of a coordinate system noted in the following relate to the illustration in the attached drawings and serve only to describe the invention.

If the invention is described essentially with reference to a positive model, this does not, however, restrict the invention. The same applies analogously to a plaster model.

In the first embodiment, a positive model in the form of a wax model 1 of a dental bridge is clamped in a mounting 2 of a device according to the invention, as shown in the figures. The mounting 2 is mounted on a shaft 3 which enables a rotation of the mounting 2 by 180°. Furthermore, the shaft 3 is mounted on a table 4 which can travel precisely in three axes x, y, z. The axis of rotation of the shaft 3 extends, for example, in the y direction. The drive of the table 4 is mounted in an equipment housing 5. The opening in the equipment housing 5 required for the travel movement of the table 4 can be covered in any known manner, e.g. by a bellows or by a sleeve 6.

Furthermore, an optical scanning unit 7 is accommodated in the equipment housing 5 for measuring distance. The scanning unit 7 comprises a laser beam source (not shown in greater detail), e.g. a laser diode, as well as advantageously a device for reflecting the light of the laser diode into the ray path of the scanning unit 7 and further optical elements as well as a CCD camera adjusted in its sensitivity to the laser. A birefractive crystal which splits the laser light reflected by the wax model 1 (positive model) into a regular portion and an irregular portion is arranged in front of the CCD camera, as a result of which holograms with border areas are generated on the CCD image recorder which can be accurately measured and with reference to which the exact distance to the measured point can be determined.

The scanning unit 7 is fastened in the equipment housing 5 in such a way that an emitted laser beam runs along the z axis. After a single calibration during assembly, the scanning unit 7 delivers absolute information about the distance to an object reflecting the laser beam, e.g. a wax model 1 (positive model) clamped in the mounting 2, according to the so-called conoscopic holography. Details of this measuring method are described, for example, in WO 99/64916, U.S. Pat. No. 5,953, 137, WO 99/42908, U.S. Pat. No. 5,892,602, U.S. Pat. No. 5,291,314, EP 0 394 137, EP 0 394 138 and U.S. Pat. No. 4,976,504.

The high intensity of the laser light enables the use of an image forming objective with a relatively small opening, so that a field depth is produced which is larger than, for example, the typical height of a dental bridge or the wax model 1 thereof or the dental stump of a plaster model, e.g. 15 mm.

Since the previously described scanning unit 7 gives measured values about the absolute distance of the point lit by the laser beam based on the reflection as measured value, when mounting a device according to the invention, not only is the scanning unit 7 adjusted such that the laser beam is parallel to the z axis of the table 4, but the scanning unit 7 is also calibrated via a reference plate which is clamped in the mounting 2. Thus, the area of the tolerable blur (field depth) can thereby be simultaneously determined by moving the table 4 accordingly in the z direction.

During a later mapping of the positive model 1 such as the wax model or plaster model, the mounting 2 is moved over the table 4 along the z axis of the table 4, accordingly in the focus range of the scanning unit 7. The plaster or positive model 1 is now digitalized by moving the mounting 2 and the table 4 in a defined manner along the x and y axis, e.g. by line or in columns, and this information is linked with the distance information determined by the scanning unit 7. The position of the table 4 and with it of the model 1 to be mapped in the z direction, is subtracted from the distance value which the scanning unit 7 gives to form the measured data set. During scanning of the model 1, the table 4 is not moved along the z axis but only in x and y direction.

By linking the x and y position values with the distance information of the scanning unit 7, a data pattern is produced which reproduces the three-dimensional design of the side of the plaster or positive model 1 facing the scanning unit 7.

For the complete three-dimensional appraisal of the entire model 1, the positive model 1 together with the mounting 2 is turned about the y axis through 180° after one side has been scanned and the rear side of the positive model 1 is mapped in the same manner.

However, a prescan (preliminary run-through of the method) can also be undertaken prior to starting the measurement of the first side of the positive model 1 to determine an extreme value of the positive model 1 in the z direction, e.g. the model point with the least distance to the scanning unit 7 and the associated z value of the coordinate as reference value and thus the distance information standardized to the model point as reference point. This reference value can be adopted for forming a reference plane perpendicular to the z axis. In this way, the maximum extents of the mapped model can be derived directly from the data set generated.

If redundant measured data is generated by the mapping of two sides, these can be removed later by appropriate reprocessing by software when forming the volume model to avoid malfunctions during later control of a processing machine or a processing tool such as a milling tool 8.

A milling tool 8 of this type is advantageously integrated in a housing 5, for example, relative to the table 4, opposite the optical scanning unit 7. Advantageously, the milling tool 8 has a stationary spindle. A ceramic blank 9, for example, consisting of a presintered yttrium oxide stabilized zirconium oxide, is clamped in a further mounting 10 which is connected with the rear end of the shaft 3. The forward movements in the x, y and z directions required for processing the side of the blank 9 facing the milling tool 8 are carried out by corresponding movement of the table 4 with the shaft 3 and the mounting 10. When the processing of the side of the blank 9 facing the milling tool 8 is finished, the blank 9 can be moved away from the milling tool 8 in z direction by a forward movement and the mounting 10 turned by 180°, as during scanning of the positive model 1, to process the other side of the blank 9.

Instead of a ceramic blank 8, a blank consisting of any other suitable material, e.g. a metal, plastics or composite materials, can also be used.

In a further embodiment of the invention (not shown in the figures), the use of a so-called line scanner is provided instead of the laser beam with almost point-like cross section, whereby the line width should correspond to at least the width of the model to be scanned, e.g. in the order of 100 mm. With a line scanner of this type, which can, moreover, work similarly to the scanning unit 7 already described above, it would then be possible to completely digitalize three-dimensionally a positive model 1 or also a plaster stump or a plaster model of the jaw by moving the table 4 with the mounting 2 and the plaster or positive model 1 along an axis. If a positive model is scanned, both sides are measured by turning the mounting through 180°. With a plaster model, only the side with the dental stumps is scanned.

For example, a wax model of a bridge construction, which has three-dimensionally formed functional or connecting surfaces both on the upper side and on the lower side, scanned from both sides by a line scanner of this type after a rotation of the mounting through 180°, as previously noted.

The scanning of a three-dimensional plaster or positive model 1 according to the invention by displacement along only one or at most two axes, with an additional turning of the model 1 through 180°, also represents, with respect of the computational effort required to form a three-dimensional data model of the measured object, significant progress compared to the known optical scanning devices, in which the object to be scanned is usually tilted several times and the data pattern of the various "views" thus obtained must be linked with one another by appropriate computational operations to produce a volume model of the measured object.

However, care must be taken that, for a sufficiently reliable reflection and thus a reliable distance adjustment by the scanning unit 7 with typical materials for the modelling in the dental field, the surfaces to be mapped form an angle of at least about 0.1°, preferably of at least 1°, to the z axis with the optical axis of the laser beam. Nevertheless, the angle should not exceed 20°. However, this does not represent a limitation in practice since, at the latest for mounting the dental prosthesis onto the prepared tooth stump or the implant, at least such an inclination is required for the proper cementing of the prosthesis as would be required for a shape inclination of a conventional cast prosthesis. Undercuts may not occur in any event in prostheses of these types, since cavities between the prosthesis and tooth stump could form in this case, which would inevitably lead to further damage of the tooth stump, for example, by caries bacteria remaining in the cavity thus produced.

To ensure a sufficiently accurate clamping of the plaster or positive model 1 to be mapped in the mounting 2, this can, for example, be accomplished with aid of a parallelometer, in which an apparent undercut, caused by an inclined position of the model or a tangential run of the laser beam of the scanning unit 7, can be prevented with very good reliability and reproducibility with aid of the adjustment of the so-called light-gap method.

It is understood that it can also be provided that the scanning unit 7 moves in the z direction instead of the table 4 being moved in the z direction or even that a movement in the z direction can be entirely omitted for the scanning if the scanning unit 7 is equipped with interchangeable objectives of various focus lengths for adapting the working distance or with a zoom optic having an adjustable focal length.

The invention claimed is:

1. Method for the three-dimensional mapping and digitization of a plaster or positive model (1), for producing a dental prosthesis, with the following steps:

clamping the plaster or positive model (1) in a mounting frame (2) which is rotatable about an axis of rotation in a defined orientation;

irradiating of the plaster or positive model (1) by means of a radiation source and receiving the radiation reflected by the plaster or positive model (1);

evaluating the reflected radiation by a scanning unit (7) and generating a distance information;

positioning the mounting frame in a plane running parallel to the x- and y- axes of a Cartesian coordinate system;

definedly moving the plaster or positive model (1) relative to the radiation source along a first axis (y) which extends perpendicular or almost perpendicular to the direction of radiation;

definedly moving the mounting frame (2) with the plaster or positive model relative to the radiation source along a second axis (x-axis) extending both perpendicularly or almost perpendicularly to the first axis (y-axis) and perpendicularly or almost perpendicularly to the direction of radiation;

linking the second travel path with the distance information and the second travel path;

linking a signal for detection of the rotation with the path and distance information for forming a three-dimensional volume model of the plaster or positive model (1), whereby the distance between the mounting (2) and scanning unit (7) in direction of the optical axis (z axis) of the scanning unit (7) remains unchanged or essentially unchanged during the digitization of the plaster or positive model (1) along a scanning path, where the length of the path is greater than or equal 1 mm.

2. Method according to claim 1, characterized in that the distance between the mounting frame (2) and the scanning unit (7) along the entire or almost entire scanning path s of a side of the plaster or positive model is constant.

3. Method according to claim 1, characterized in that, to determine and digitalize the plaster or positive model, it is turned through 180° or approximately 180° about the axis of rotation of the mounting which extends perpendicular to the direction of radiation.

4. Method according to claim 1, characterized in that the radiation takes place by a line scanner.

5. Method according to claim 1, characterized in that the radiation takes place by a laser beam with almost point-like beams.

6. Method according to claim 1, further characterized by the following step:

standardizing the distance information to a reference point of the plaster or positive model (1).

7. Method according to claim 6, characterized in that the reference point is almost that point of the plaster or positive model (1) which delivers the lowest distance value.

8. Method according to claim 6, characterized in that the reference point is determined by a preliminary run-through of the method.

* * * * *